United States Patent [19]
Grabenkort et al.

[11] Patent Number: 5,876,372
[45] Date of Patent: Mar. 2, 1999

[54] SYRINGE SYSTEM ACCOMODATING SEPERATE PREFILLED BARRELS FOR TWO CONSTITUENTS

[75] Inventors: Richard W. Grabenkort, Barrington; John M. Hofstetter, Vernon Hills; John A. O'Neil, Mundelein, all of Ill.

[73] Assignee: Abbott Laboratories, Abbott Park, Ill.

[21] Appl. No.: 916,903

[22] Filed: Aug. 21, 1997

Related U.S. Application Data

[63] Continuation of Ser. No. 722,603, Sep. 27, 1996, abandoned, which is a continuation-in-part of Ser. No. 408,463, Mar. 22, 1995, Pat. No. 5,569,193.

[51] Int. Cl.⁶ ............................................. A61M 37/00
[52] U.S. Cl. ................................. 604/89; 604/91
[58] Field of Search .................... 64/87–92, 191, 64/187, 232, 218

[56] References Cited

U.S. PATENT DOCUMENTS

| | | |
|---|---|---|
| 2,475,939 | 7/1949 | Applezweig . |
| 3,255,752 | 6/1966 | Dick . |
| 3,477,432 | 11/1969 | Shaw ........................................ 604/91 |
| 3,489,147 | 1/1970 | Shaw . |
| 3,621,843 | 11/1971 | Metten . |
| 3,678,931 | 7/1972 | Cohen . |
| 3,682,174 | 8/1972 | Cohen . |
| 3,754,644 | 8/1973 | Hampel . |
| 3,757,779 | 9/1973 | Rovinski . |
| 3,838,689 | 10/1974 | Cohen . |
| 4,153,057 | 5/1979 | Kobel . |
| 4,171,698 | 10/1979 | Genese . |
| 4,172,457 | 10/1979 | Choksi et al. . |
| 4,243,080 | 1/1981 | Choksi et al. . |
| 4,581,016 | 4/1986 | Gettig . |
| 4,581,023 | 4/1986 | Kuntz . |
| 4,840,616 | 6/1989 | Banks . |
| 4,936,315 | 6/1990 | Lineback . |
| 4,957,637 | 9/1990 | Cornell .................................. 604/89 X |
| 5,067,998 | 11/1991 | Singh et al. . |
| 5,088,996 | 2/1992 | Kopfer et al. ........................ 604/87 X |
| 5,114,405 | 5/1992 | Winter . |
| 5,125,892 | 6/1992 | Drudik . |
| 5,135,507 | 8/1992 | Haber et al. . |
| 5,158,546 | 10/1992 | Haber et al. ............................... 604/87 |
| 5,176,639 | 1/1993 | Pozzi et al. . |

(List continued on next page.)

FOREIGN PATENT DOCUMENTS

| | | |
|---|---|---|
| 0 005 939 | 12/1979 | European Pat. Off. . |
| 0 298 585 | 1/1989 | European Pat. Off. . |
| 0 302 248 | 2/1989 | European Pat. Off. . |
| 0 599 649 A1 | 6/1994 | European Pat. Off. . |
| 0 695 555 A1 | 2/1996 | European Pat. Off. . |
| WO 92/01485 | 2/1992 | WIPO . |
| WO 92/10225 | 6/1992 | WIPO . |
| WO 96 29106 | 9/1996 | WIPO . |
| WO 96/30066 | 10/1996 | WIPO . |

*Primary Examiner*—John D. Yasko
*Attorney, Agent, or Firm*—Neal D. Marcus

[57] ABSTRACT

A prefilled, two-constituent system is provided with first and second containers or barrels. The first barrel includes a first chamber having a dispensing end or delivery end. The delivery end defines a dispensing passage or delivery passage communicating through the delivery end to accommodate the dispensing of fluid from the first chamber. A movable seal or reciprocable stopper is slidably disposed in the first chamber, and a first constituent is provided in the first chamber between the delivery end and the stopper. A second container or barrel is sized to be disposed in the first barrel and has a discharge end defining a discharge passage communicating through the discharge end to accommodate the discharge of fluid from the second barrel. A plunger is slidably disposed within the second barrel. A liquid second constituent is provided in the second barrel between the discharge end and the plunger. The first barrel stopper and the second barrel discharge end are engageable directly or indirectly to cooperatively define a coupling accommodating the flow of the liquid second constituent from the second barrel into the first chamber of the first barrel as the second barrel moves outwardly relative to the first chamber.

20 Claims, 4 Drawing Sheets

U.S. PATENT DOCUMENTS

| | | | |
|---|---|---|---|
| 5,181,909 | 1/1993 | McFarlane . | |
| 5,289,858 | 3/1994 | Grabenkort . | |
| 5,298,024 | 3/1994 | Richmond . | |
| 5,372,586 | 12/1994 | Haber et al. ............................. | 604/89 |
| 5,407,431 | 4/1995 | Botich et al. . | |
| 5,472,431 | 12/1995 | Godat et al. . | |
| 5,496,288 | 3/1996 | Sweeney . | |
| 5,520,657 | 5/1996 | Sellers et al. . | |
| 5,569,193 | 10/1996 | Hofstetter et al. . | |

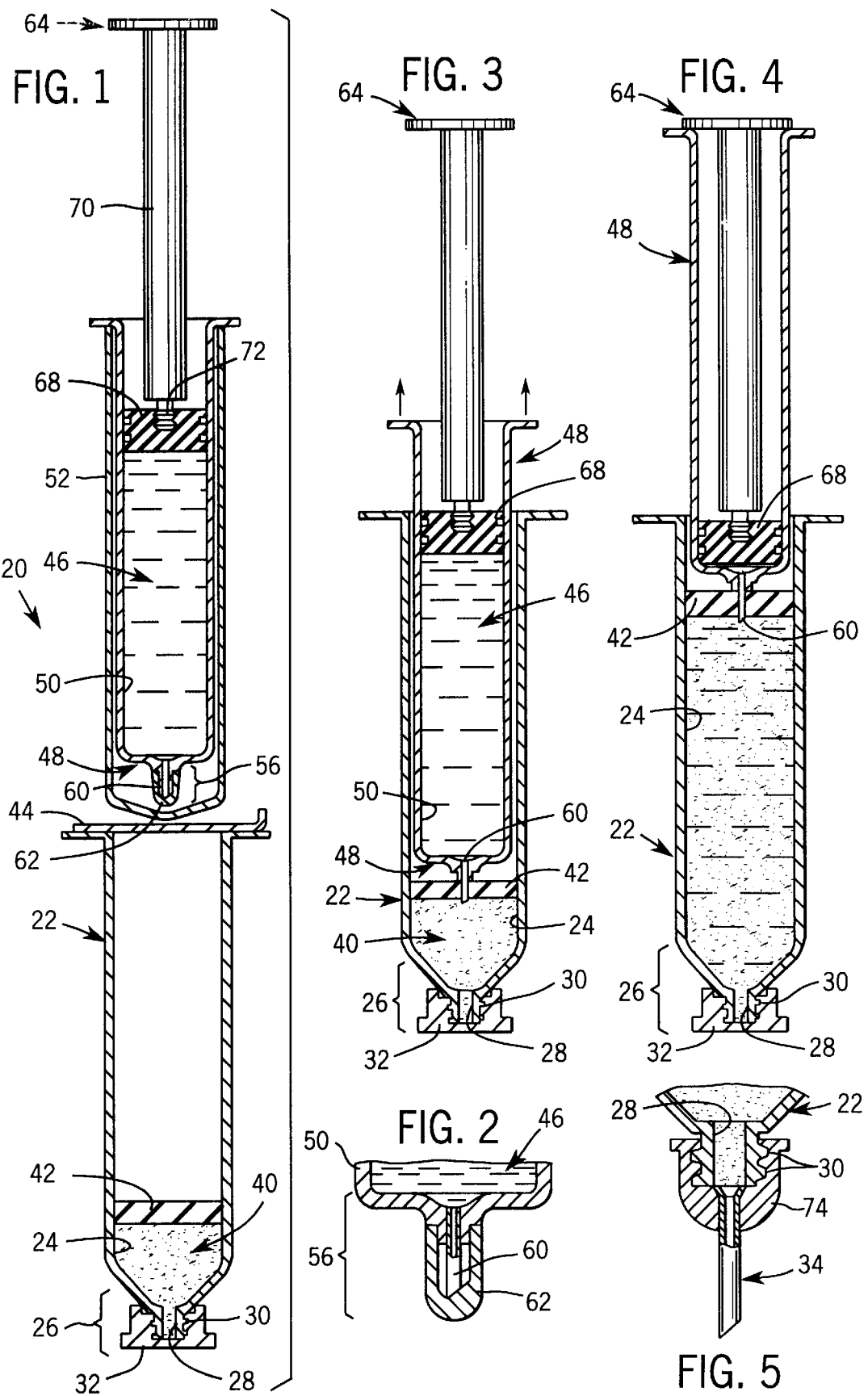

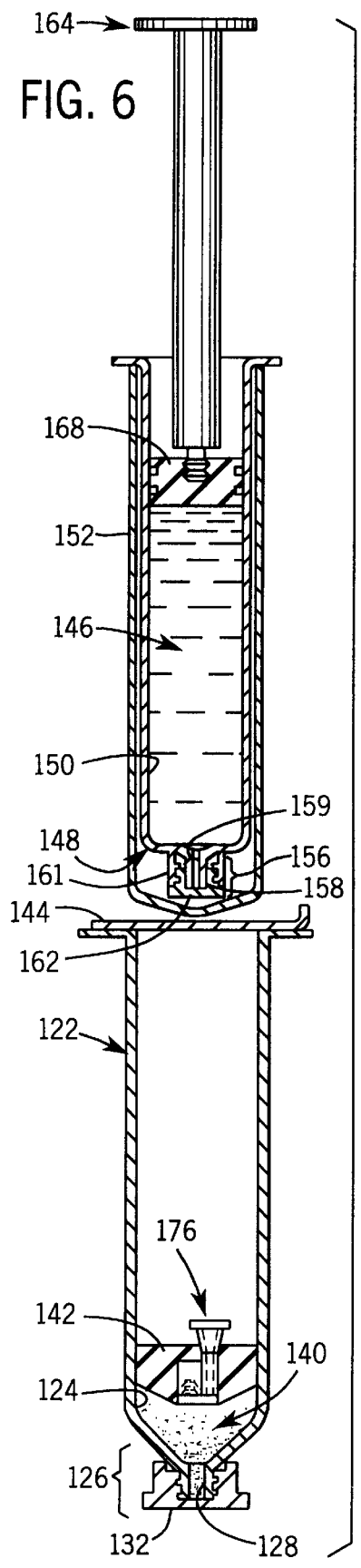
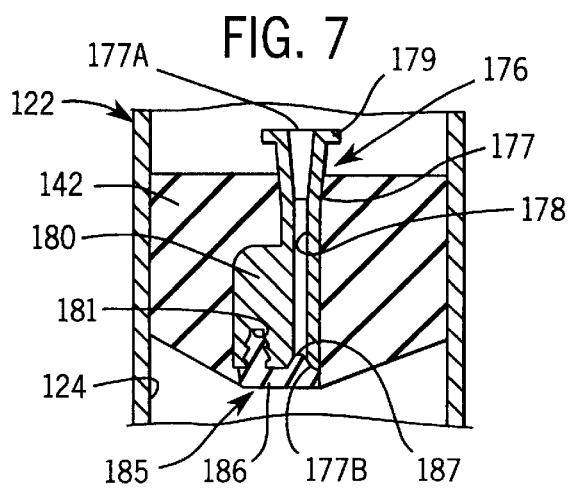
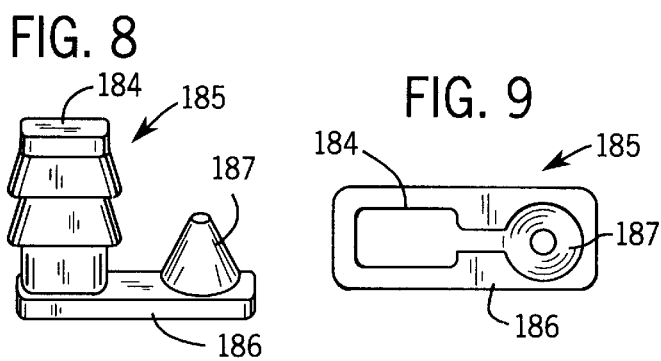
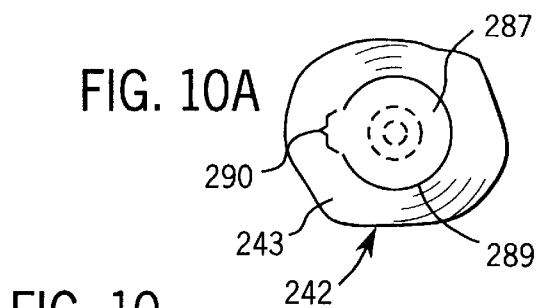
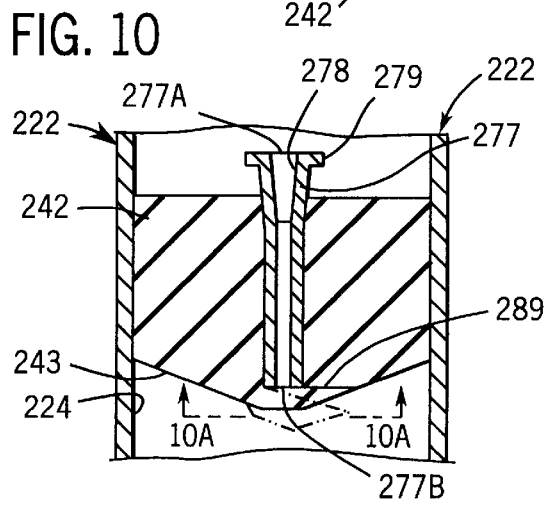

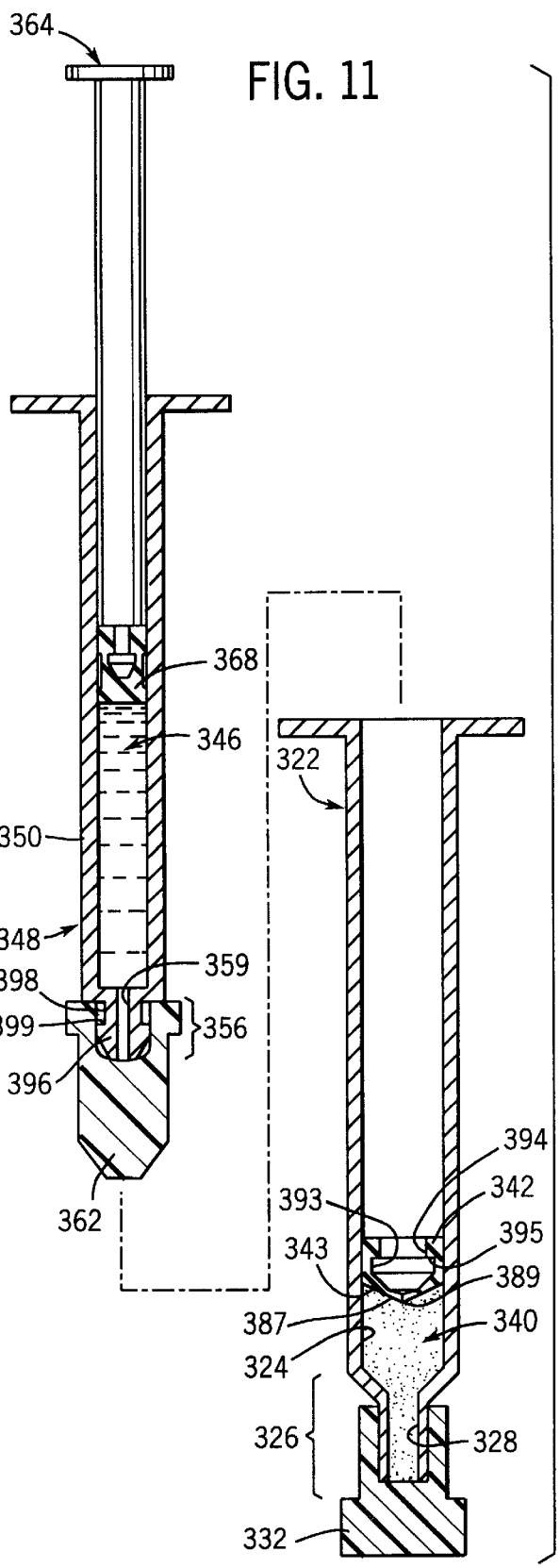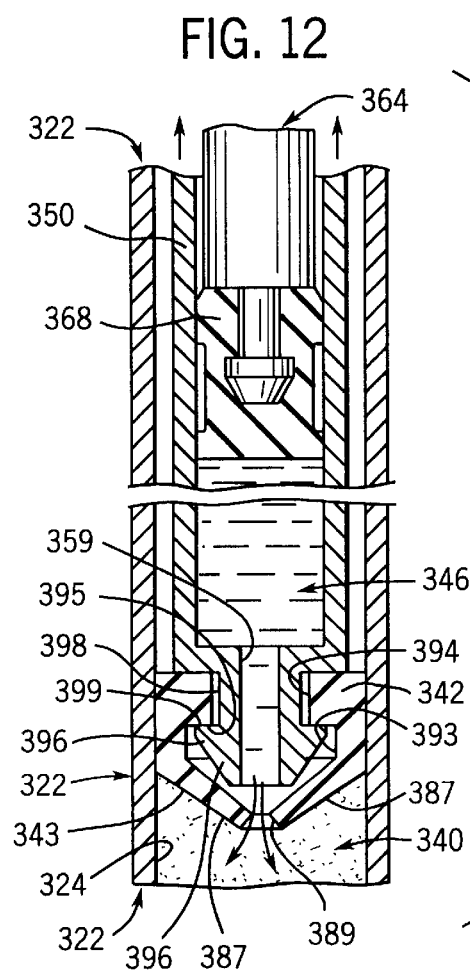

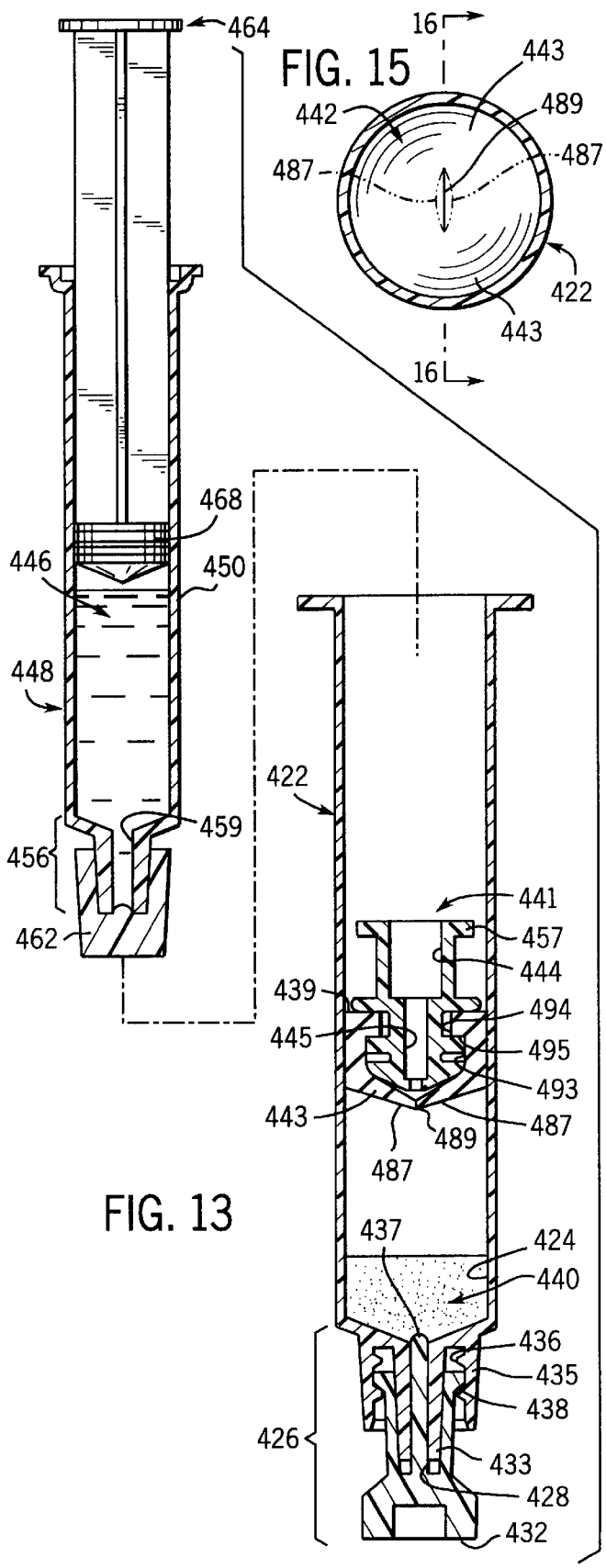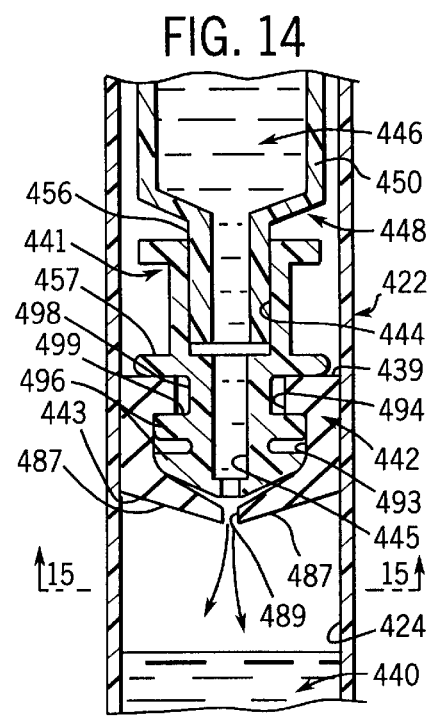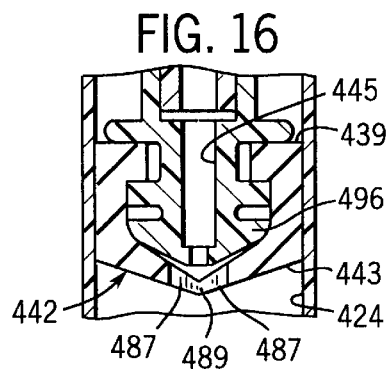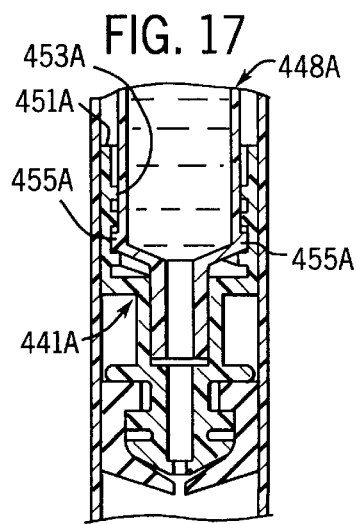

SYRINGE SYSTEM ACCOMODATING SEPERATE PREFILLED BARRELS FOR TWO CONSTITUENTS

This application is a continuation of Ser. No. 08/722,603, filed Sep. 27, 1996 now abandoned which is a Continuation In Part of Ser. No. 08/408,463, filed Mar. 22, 1995.

TECHNICAL FIELD

This invention relates to a syringe system for packaging, mixing and delivering two constituents or components that are stored separately in isolation from each other but which must be combined or mixed together prior to delivery. The invention is particularly suitable for use with a medicament, such as a drug in powder form, which must be dissolved and diluted in a liquid prior to delivery.

BACKGROUND OF THE INVENTION AND TECHNICAL PROBLEMS POSED BY THE PRIOR ART

In some medical applications, as well as in some industrial or other applications, it is necessary, or at least preferable, to maintain two components or constituents in isolation prior to combining the two components for subsequent delivery as a solution, mixture, or other combination.

For example, some pharmaceutical preparations, such as injectable solutions or suspensions of a drug, are not sufficiently stable to accommodate prolonged storage prior to use. However, the components of the solution or suspension may have adequate stability if the components are stored separately prior to being combined.

It would be desirable to provide an improved syringe system that will accommodate the packaging of two such components in isolation from each other, but which can be subsequently operated to combine or mix the components for delivery. In particular, it would be advantageous to provide such an improved syringe system with the capability, where necessary, for employing component prefilled barrels that can be manufactured and/or stored separately as well as together.

It would be especially advantageous if such an improved system could be employed with two liquid components as well as with at least one solid component.

It would be desirable with such a system to positively seal both components from the ambient atmosphere as well as from each other.

It would also be beneficial if such an improved system could be provided in a self-contained form that is compact, portable, simple to manipulate, and readily adaptable to different proportions and dosages of the components.

Additionally, it would be desirable if such an improved system could readily accommodate the storage, mixing and administration of a variety of drugs which require reconstitution and/or dilution including, among other types, a medicament in powder form requiring mixing with a diluent, a medicament in liquid form requiring mixing with a diluent, and a lyophilized compound requiring mixing with a diluent.

The present invention provides an improved packaging, mixing and delivery system which can accommodate embodiments having the above-discussed benefits and features..

SUMMARY OF THE INVENTION

The present invention provides a syringe system for storing two components or constituents in isolation from each other. The system can be subsequently operated for combining or mixing the two constituents and for then delivering the combination.

The syringe system includes first and second prefilled containers which each includes first and second prefilled syringe barrels, respectively. The first barrel includes an open end and an opposite substantially closed delivery end. The delivery end defines a delivery passage or dispensing passage to accommodate the delivery or dispensing of fluid from the first barrel. Preferably, a first removable closure is provided to occlude the delivery passage. A reciprocable stopper or moveable seal is slidably disposed in the first barrel to define a first chamber. The first chamber is preferably prefilled with a first constituent between the reciprocable stopper and the delivery end.

The second barrel is sized to be disposed in the first barrel and has an open end and an opposite substantially closed discharge end having a discharge passage to accommodate the discharge of fluid from the second barrel. Preferably, a second removable closure is provided to occlude the discharge passage. A slidable plunger is sealingly disposed within the second barrel to define a second chamber. The second barrel is preferably prefilled with a liquid second constituent in the second chamber between the discharge end and the slidable plunger.

In order to combine the two constituents, the second closure, if any, is first removed from the second barrel discharge end. The first barrel reciprocable stopper and the second barrel discharge end are engageable to cooperatively define a coupling or fluid transfer connector means for accommodating the flow of the liquid second constituent from the second chamber into the first chamber. This can include (a) connecting means for connecting the second barrel with the reciprocable stopper in the first barrel, and (b) fluid communicating means for establishing fluid communication between the first and second chambers. As the second barrel discharge end and plunger are moved closer together, the liquid constituent is moved (i.e., pushed) from the second chamber into the first chamber where the liquid second constituent mixes with the first constituent. The assembly may be shaken to promote mixing.

Subsequently, the first closure can be removed from the first barrel. Then the second barrel, which is engaged with the reciprocable stopper, can be pushed inwardly. This movement carries both the second barrel and coupled reciprocable stopper inwardly into the first chamber. This coupled movement dispenses the mixed contents of the first chamber through the delivery passage.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is a partial cross-sectional view of a first embodiment of the syringe system of the present invention showing the first and second containers before the container barrels are coupled together;

FIG. 2 is a greatly enlarged, fragmentary, cross-sectional view of the discharge end of the second barrel;

FIG. 3 is a view of the components of FIG. 1 in a coupled condition with the reciprocable stopper in the first barrel penetrated by the piercing needle of the second barrel just prior to the plunger of the second barrel being moved toward the discharge end;

FIG. 4 is a view similar to FIG. 3, but FIG. 4 shows the liquid contents of the second barrel completely discharged into the first barrel;

FIG. 5 is a greatly enlarged, fragmentary, cross-sectional view of the delivery end of the first barrel shown with the first closure removed and replaced with a needle;

FIG. 6 is a cross-sectional view of a second embodiment of the present invention showing the separate first and second barrels of the containers prior to being coupled together;

FIG. 7 is a greatly enlarged, fragmentary, cross-sectional view of the conduit assembly and reciprocable stopper in the first barrel of the second embodiment;

FIG. 8 is a perspective view of the valve member employed in the reciprocable stopper of the second embodiment;

FIG. 9 is a top plan view of the valve member shown in FIG. 8;

FIG. 10 is a view similar to FIG. 7, but FIG. 10 shows a third embodiment of the present invention having a modified reciprocable stopper;

FIG. 10A is a fragmentary, bottom plan view taken along the plane 10A—10A in FIG. 10;

FIG. 11 is a cross-sectional view of a fourth embodiment of the present invention showing the separate first and second barrels of the containers prior to being coupled together;

FIG. 12 is a greatly enlarged, fragmentary, cross-sectional view of a portion of the assembled components of the fourth embodiment showing the second barrel being operated to open the mixing valve of the first barrel;

FIG. 13 is a cross-sectional view of a fifth embodiment of the present invention showing the separate first and second barrels of the containers prior to being coupled;

FIG. 14 is a greatly enlarged, fragmentary, cross-sectional view of a portion of the assembled components of the fifth embodiment showing the second barrel being operated to open the mixing valve of the first barrel;

FIG. 15 is a cross-sectional view taken generally along the plane 15—15 in FIG. 14;

FIG. 16 is a cross-sectional view taken generally along the plane 16—16 in FIG. 15; and FIG. 17 is a fragmentary, cross-sectional view of a portion of the assembled components of a sixth embodiment of the present invention showing the second barrel being operated to open the mixing valve in the first barrel.

DESCRIPTION OF THE PREFERRED EMBODIMENT

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

Figures illustrating the apparatus show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

A first embodiment of the prefilled syringe system of the present invention is illustrated in FIGS. 1–5 and is designated generally therein by the reference number 20. The system may be generally characterized as including two "containers" for separately storing two constituents or components in isolation from each other, but which can be subsequently operated to combine or mix the components for delivery. The first container includes a first barrel 22 having an open end 24 and an opposite, substantially closed, dispensing end or delivery end 26 defining a delivery passage or dispensing passage 28. The first barrel 22 is preferably fabricated from a synthetic polymer, such as a thermoplastic material, but the barrel may be made of other suitable material such as glass.

A first constituent or component 40 is provided in the first barrel 22. The constituent 40, in the preferred embodiment contemplated for use in medical applications, can be a drug or other medicament in granular form, powder form, or other particulate form. The first constituent may also be a liquid. It is contemplated that the constituent 40 in the first barrel 22 would typically be a drug which, if in solid form, requires reconstitution, or if in liquid form, requires dilution. Thus, the system of the present invention will be useful in the containment of hazardous drugs such as are used in oncological applications or in biotechnology delivery applications.

Preferably, the delivery end 26 defines an exterior thread form 30 for receiving a threaded cap or first removable closure 32 and for subsequently receiving, upon removal of the closure 32, a suitable dispensing component, such as a hollow needle 34 described hereinafter in detail with reference to FIG. 5. Any other suitable conventional or special capping system may be employed.

A reciprocable stopper 42 is slidably disposed in the first chamber 24 above the first constituent 40. Preferably, the reciprocable stopper 42 is fabricated from a resilient, elastomeric material. In the preferred form, the reciprocable stopper 42 has an uncompressed diameter somewhat larger than the diameter of the chamber 24. A friction-fit engagement is established between the stopper 42 and the chamber 24 that is sufficient to hold the stopper 42 in place on top of the constituent 40 during normal packaging, shipping and handling. However, the force of engagement is sufficiently low to permit sliding of the stopper 42 along the chamber 24 when the stopper 42 is subjected to a sufficiently high axial force as described in detail hereinafter.

The reciprocable stopper 42 may be alternatively described as a moveable seal, slidable seal, piston, or grommet. All of these terms may be regarded as interchangeable herein. The term "moveable seal" has been used in the above-identified parent patent application Ser. No. 08/408, 463. However, the term "reciprocable stopper" is generally used herein to define the same or analogous components.

As illustrated in FIG. 1, it is also preferred to provide an outer cover 44 over the upper, open end of the first container barrel 22. This prevents ingress of contaminants. The cover 44 may be an adhesive backed, flexible web that can be readily pulled off just prior to use of the system.

The first barrel 22 may be regarded as a first container together with the closure 32, stopper 42, and cover 44 for storing the first component 40 and subsequently mixing the first component 40 with another component as explained in detail hereinafter.

A second constituent or component 46, in the form of a liquid, is sealed within a second barrel 48. The liquid constituent 46 would typically be a diluent for diluting and/or reconstituting the first constituent 40. The second barrel 48 may be formed from the same synthetic polymer materials as used for the first container 22.

The second barrel 48 preferably includes a generally cylindrical wall portion 50 that is sized to be disposed in the first container 22 (FIGS. 3 and 4). Initially, in the pre-assembled condition, the second barrel 48 is preferably encased in a protective sleeve 52 which must be removed prior to use.

The second barrel 48 also includes a plunger assembly or plunger assembly or plunger 64 which is slidably disposed within the cylindrical barrel 50. The plunger 64 includes a plunger shank or stem 70 with a thumb push flange at one end and a piston 68 at the other end slidably received within the barrel cylindrical wall portion 50.

The piston 68 is preferably elastomeric and is initially located at the upper end of the second barrel 48 in contact with the liquid second constituent 46 as illustrated in FIG. 1. For packaging convenience, the plunger shank 70 may be provided with a threaded end or snap-fit end 72 for engaging a mating thread form or snapfit form in the top of the piston 68. Such a structure permits packaging of the system components with the plunger shank 70 not initially connected or assembled with the piston 68. When it is subsequently desired to use the system, the user can thread or snap-fit the shank 70 into the piston 68.

The second barrel 48 has a discharge end 56 defining a discharge passage communicating through the discharge end to accommodate the discharge of fluid from the barrel 48. In the first embodiment illustrated in FIGS. 1–5, the second barrel discharge passage is defined by the hollow interior of a piercing needle 60 which is mounted in the discharge end of the second barrel 48.

Preferably, the second barrel 48 is initially provided to the user with a second cap or removable closure 62 mounted to the second barrel discharge end 56 over the piercing needle 60 as shown in FIG. 2. The second closure 62 may be held on the discharge end of the second container by means of a snap-fit (or by other means, e.g., a threaded engagement (not illustrated).

The second barrel 48 may be regarded as a second container together with the closure 62 and plunger 64 for storing and subsequently functioning as a syringe to discharge the liquid second constituent 46 into the first container barrel 22 as will be explained in detail hereinafter.

The operation of the packaging syringe system 20 will next be described with reference to the sequential operational steps illustrated in FIGS. 3–5. The first stage of the operation is illustrated in FIG. 2.

Just prior to use, the second closure 62 is removed to expose the piercing needle 60. Preferably, before the second closure 62 is removed, the second barrel 48 is inverted (so that the piercing needle 60 is pointing generally upwardly). This will ensure that the liquid constituent 46 cannot drip out. However, even if the second barrel 48 is not inverted, the liquid constituent 46 will not drip out. This is because the second barrel 48 has no vent system. A vent system would admit ambient air into the second barrel 48 so as to permit the liquid constituent to flow out through the needle 60 solely under the influence of gravity. Without such venting, the liquid constituent 46 remains in the second barrel 48 and is not able to flow out through the piercing needle 60.

With the second barrel 48 preferably inverted to point the piercing needle 60 upwardly, the first barrel 22 is inverted and aligned with the second barrel 48. Then relative movement is effected so as to locate the distal end of the second barrel 48 in the first barrel 22. As illustrated in FIG. 3, the second barrel 48 is inserted into the first barrel 22 until the piercing needle 60 engages, and penetrates completely through, the reciprocable stopper 42 of the first barrel 22.

Before and during the step of inserting the second barrel 48 inside the first barrel 22, the moveable plunger 64 is not moved relative to the second container 48. The plunger 64 remains in the initial, outermost orientation. After the two barrels are telescopically disposed with the piercing needle 60 fully penetrating the stopper 42 in the first barrel 22, the plunger 64 is pushed inwardly within the second barrel 48 (i.e., toward the discharge passage in the needle 60 of the second barrel 48). The plunger movement causes the liquid second constituent 46 to flow out through the hollow piercing needle 60 to mix with the first constituent 40 within the first chamber 24. The hydraulic pressure within the first chamber 24 acts on the stopper 42 and the abutting distal end of the second barrel 48. The increasing pressure moves (i.e., pushes) the reciprocable stopper 42 and the second barrel 48 outwardly relative to the first barrel 22. It will be appreciated that the ambient atmospheric pressure bears on the outside surface of the plunger piston 68, and this additional pressure is effective in aiding the discharge of the liquid second constituent 46 into the first chamber 24.

When the piston 68 is seated at the bottom, discharge end of the second barrel 48, the top, open end of the second barrel 48 is adjacent to the thumb push flange at the top of the plunger 64 (as shown in FIG. 4). Substantially all of the liquid second constituent has been discharged through the hollow piercing needle 60 into the first chamber 24 of the first barrel 22 where it forms a solution with, mixes with, or is otherwise combined with the first constituent 40. The assembly can be shaken to ensure good mixing.

After the constituents are sufficiently mixed, the first closure 32 is removed from the first barrel 22, and the delivery end 26 can be connected to a receiving component or discharge component, such as a flexible container or tubing set (not illustrated). Optionally, a hollow needle 34 is mounted at the distal end of the first barrel delivery end 26. The needle 34 may be of a conventional, single-ended type with a straight, hollow, stainless steel shaft, typically 20 gauge in size. The needle 34 may be provided with a swaged or molded hub 74 (FIG. 5) for engagement with the bottom, distal end of the delivery end 26 of the first barrel 22.

When properly mounted on the first barrel 22, the needle 34 is in alignment with the delivery passage 28, and fluid communication is established between the delivery passage 28 and the needle 34. After the needle 34 is properly mounted on the first barrel 22, (or after the first barrel 22 is otherwise properly connected to some suitable receiving component), the plunger 64 and second barrel 48 can be moved forward by applying an axial force. This causes the combined constituents in the first chamber 24 to be dispensed or expelled from the chamber 24 through the needle 34.

It will be appreciated that the first barrel stopper 42 has a central portion which is fully penetratable by the needle 60. That stopper central portion and the second barrel piercing needle 60 cooperatively define a fluid transfer connector means or coupling means incorporating (a) fluid communicating means and (b) connecting means. The fluid communicating means includes the flow passage through the needle 60 which is operative to accommodate the flow of the liquid second constituent from the second barrel 48 into the first chamber 24 of the first barrel 22. The connecting means includes the sealing engagement between the exterior of the needle 60 and the stopper 42 which accommodates the movement of the stopper 42 together with the second barrel 48—first outwardly as the liquid second constituent 46 is moved (i.e., forced or pushed) into the first chamber 24, and subsequently inwardly outwardly into the first chamber 24 to dispense the combined constituents.

An alternate second embodiment of the syringe system of the present invention is illustrated in FIGS. 6–9. Elements in the alternate embodiment which are the same as, or which function in an analogous manner to, elements of the first-embodiment illustrated in FIGS. 1–5 are designated with three digit reference numbers wherein the last two digits are the same as the two digits of the reference number of the corresponding element in the first embodiment.

With reference to FIG. 6, the second embodiment of the syringe system includes a first barrel 122 and a second barrel 148. The first barrel 122 has an open upper end which is initially sealed with a removable cover 144. The first barrel 122 contains a first component or constituent 140. The first constituent 140 is deposited in the bottom of the first barrel 122 which defines a dispensing end or delivery end 126 having a dispensing passage or delivery passage 128 communicating through the dispensing end or delivery end 126 to accommodate the dispensing of fluid from the first chamber 124.

The closed delivery end 126 preferably includes a concentrically extending collar with an interior threaded form for receiving a first removable closure 132 as shown in FIG. 6. Upon removal of the closure 132, the delivery end 126 can be threadably mated with a suitable receiving component, such as a stopcock or an IV administration set (not illustrated).

A reciprocable stopper 142 is slidably disposed in the first barrel 122 and, together with the first barrel 122, defines a first chamber 124 which is initially filled with the first constituent 140. The stopper 142 is retained with sufficient frictional engagement to prevent its movement within the first barrel 122 during normal storage, transport, and handling.

The reciprocable stopper 142 may be alternatively described as a moveable seal, slidable seal, piston, or grommet. All of these terms may be regarded as interchangeable herein. The term "moveable seal" has been used in the above-identified parent patent application Ser. No. 08/408,463. However, the term "reciprocable stopper" is generally used herein to define the same or analogous components.

Preferably, the reciprocable stopper 142 is fabricated from a resilient elastomeric material. In the preferred form, the reciprocable stopper 142 has an uncompressed diameter somewhat larger than the diameter of the first barrel 122 for a friction-fit slidable engagement with the first barrel 122. The reciprocable stopper 142 is retained with sufficient frictional engagement to prevent its movement with the first barrel 122 during normal storage, transport, and handling.

As can be seen in FIG. 7, a novel conduit and valve assembly 176 is mounted in the reciprocable stopper 142. The conduit and valve assembly 176 includes a generally elongate conduit 177 (which may be in the form of a luer socket) extending through the stopper 142 and defining an internal flow passage 178 having an inlet 177A and an outlet 177B.

The conduit and valve assembly 176 includes a laterally projecting boss 180 defining a receiving cavity 181 for receiving a ribbed anchor portion 184 of a valve member insert 185. The valve member insert 185 includes a transversely oriented, resilient, spring member 186 extending from the lower end of the anchor portion 184. A frusto-conical, flapper valve member 187 projects upwardly from the spring member 186. The exterior surface of the valve member 187 is adapted to seal against the conduit outlet 177B. The spring member 186 normally biases the valve member 187 in tight sealing engagement against the conduit outlet end 177B as illustrated in FIG. 7. This defines a one-way flow valve.

The inlet end of the conduit and valve assembly 176 includes a standard female luer socket which defines the inlet 177A and from which extends a connector flange 179, such as is employed in conventional connection systems marketed under the trademark LUER-LOK. This accommodates connection of the conduit and valve assembly 176 to the second barrel 148 as described in detail hereinafter. Other suitable conventional or special connecting systems may be employed.

The first barrel 122 may be regarded as a container together with the closure 132, reciprocable stopper 142, conduit and valve assembly 176, and cover 144 for storing, and subsequently mixing, the first component 140.

The second barrel 148 is preferably initially provided with a surrounding, protective sleeve 152 which is removed and discarded subsequent to use. The second barrel 148 preferably has a cylindrical barrel portion 150 containing a liquid second constituent 146 that is retained within the barrel portion 150 by a plunger assembly or plunger 164 which includes a stem or shank having a piston 168 at one end slidably disposed within the barrel portion 150 and having a thumb push flange at the other end.

The bottom end of the second barrel 148 defines a discharge end 156. The end 156 includes an outwardly projecting discharge conduit 158 (which is preferably in the form of a standard luer nozzle) defining an internal discharge passage 159 communicating through the discharge end 156 to accommodate the discharge of fluid from the barrel portion 150 of the second barrel 148. The conduit 158 accommodates fluid-tight connection with the female luer socket which defines the inlet 177A of the conduit assembly 176 in the first barrel 122.

An axially extending collar 161 is spaced from, and surrounds, the discharge conduit 158. The collar 161 defines an internal thread form of the type that is employed in connection systems marketed under the trademark LUER-LOK. Thus, the collar 161 can be threadingly engaged with the thread flange 179 at the inlet end of the conduit and valve assembly 176 which projects from the reciprocable stopper 142 in the first barrel 122. The second barrel projecting conduit 158 is adapted to enter into the inlet 177A of the conduit and valve assembly 176 to form a leak-tight seal with the conduit 177. The second barrel collar 161 and conduit 158, and the first barrel conduit and valve assembly 176 thus function as a cooperating fluid transfer connector means or coupling means for connecting the second barrel 148 with the first barrel 122 first chamber 124 through the reciprocable stopper 142. Other suitable connection structures could be used in place of the specific form of the collar 161, conduit 158, and conduit and valve assembly 176 illustrated.

Preferably, a secondary, removable closure member 162, in the form of a threaded plug, is threadingly engaged with the collar 161, and it must be removed prior to use. This prevents ingress of contaminants and insures that the liquid second constituent will not leak out of the second barrel 148. Of course, even if the removable closure 162 is not employed, the liquid second constituent 146 cannot leak out of a small diameter passage 159 because there is no vent system that would admit ambient air into the second barrel 148 so as to permit the liquid constituent 146 to flow out solely under the influence of gravity.

The second barrel 148 may be regarded together with the closure member 162 and plunger 164 as a second container or syringe for holding, and subsequently discharging, the liquid second constituent 146.

To mix the two components, both barrels are preferably held in an inverted position. The closure 162 is removed from the second barrel 148. The second barrel 148 is inserted into the first barrel 122 to connect the second barrel discharge conduit 158 with the first barrel conduit assembly 176.

The second barrel luer nozzle conduit 158 is inserted into the female luer socket inlet 177A of the first barrel conduit and valve assembly 176. The thread in the second barrel collar 161 is then engaged with the flange 179 on the first barrel conduit and valve assembly 176. Then relative rotation between the two barrels is effected to complete the threaded engagement.

Subsequently, the second barrel plunger 164 can be pushed toward the discharge passage 159. The liquid second constituent 146 flows from the second barrel 148 through the conduit and valve assembly 176 (where the valve member 187 opens) into the first barrel 122, and the reciprocable stopper 142 moves outwardly in the first barrel 122 along with the second barrel 148 connected to the assembly 176.

The first barrel 122 and second barrel 148 could also merely be pulled outwardly relative to each other while ambient air pressure acts on the exterior surface of the plunger piston 168 and is transferred to the liquid second constituent 146. As the stopper 142 is pulled outwardly, the volume beneath the stopper 142 within the first barrel chamber 124 increases while the pressure within the chamber 124 decreases. This results in a pressure differential which opens the valve member 187 as the liquid second constituent 146 flows into the first barrel 122 to combine with the first constituent 140.

As the liquid second constituent 146 is transferred to the first barrel 122, the outward movement of the two barrels 122 and 148 relative to each other is continued until the bottom interior surface of the plunger piston 168 engages the bottom, interior surface of the second barrel 148. At this point, all of the liquid second constituent 146 has been expelled from the barrel portion 150 of the second barrel 148 into the first barrel 122. The assembly can be shaken to ensure good mixing.

The first closure 132 can then be removed from the first barrel 122, and the delivery end 126 can be connected to a suitable receiving component or discharge tubing (not illustrated). Alternatively, a needle, such as the needle 34 illustrated for the first embodiment in FIG. 5, may be attached to the first barrel 122.

Subsequently, the thumb push flange of the plunger 164 can be pushed inwardly to move the second barrel 148 and connected reciprocable stopper 142 inwardly further into the first barrel 122. This expels the combined constituents 140 and 146 from the first barrel 122.

It will be appreciated that the first barrel conduit and valve assembly 176, second barrel collar 161, and the second barrel conduit 158 cooperatively define a fluid transfer connector means or coupling means in the form of a flow-accommodating connection which permits the liquid second constituent 146 to flow from the second barrel 148 into the first barrel 122. This fluid transfer connector means or coupling means also accommodates the outward movement of the second barrel 148 relative to the first barrel 122 during the transfer of the liquid second constituent 146 from the second barrel 148 to the first barrel 122. Additionally, this fluid transfer connector means or coupling means accommodates the subsequent inward movement of the second barrel 148 during the dispensing of the combined constituents from the first chamber 124 of the first barrel 122.

The unique fluid transfer connector means or coupling means employed in the embodiment illustrated in FIGS. 6–9 may be characterized as including (1) a fluid communicating means, and (2) a cooperating connecting means.

The "fluid communicating means" includes (a) a "first fluid connector," preferably in the form of the luer-type socket or conduit 177 defining a flow passage into the first barrel 122, and (b) a cooperating "second fluid connector" in the form of the luer-type nozzle or conduit 158 defining a flow passage out of the second barrel 148.

The "cooperating connecting means" may include a friction-fit connection of luer-type nozzle or conduit 158 with the luer-type socket or conduit 177. Preferably, however, the connecting means also includes the thread form on the second barrel collar 161 and the radial flange 179 on the conduit and valve assembly 176 in the first barrel 122 to cooperatively establish a threaded connection.

A third embodiment of the present invention, which includes a modified form of the conduit and valve assembly, is illustrated in FIGS. 10 and 10A. This embodiment includes a first barrel 222 defining a first chamber 224 in which a reciprocable stopper 242 is slidably disposed above a first constituent (not visible in FIGS. 10 and 10A). A conduit 277 is mounted in the reciprocable stopper 242 and extends through the reciprocable stopper 242. The conduit 277 defines an internal passage 278 and has an inlet 277A and an outlet 277B. At the inlet 277A, the conduit 277 defines a standard female luer socket from which extends a connector flange 279 which may be identical to the flange 179 described above with reference to the embodiment illustrated in FIGS. 6–9.

The bottom of the reciprocable stopper 242 has a frusto-conical shape 243 with a partial slit 289 oriented transversely to the axis of the frusto-conical shape at a outlet 277B of the conduit 277. This slit defines a flap or valve member 287 which is attached with an unslit portion 290 (FIG. 10A) to the main body of the stopper 242. The portion 290 is resilient and normally biases the valve member 287 upwardly against the outlet 277B of the conduit 277 to occlude the passage 278.

The stopper 242 and conduit 277 illustrated in FIGS. 10 and 10A are adapted to cooperate with a second container or barrel (not illustrated) that can be identical to the second barrel 148 described above with reference to the second embodiment illustrated in FIG. 6. The second barrel can be inserted into the first barrel 222 and connected to the conduit 277 in the same manner as described above for the connection of the embodiment of the second barrel 148 with the first barrel 122 illustrated in FIG. 6. The operation of the embodiment of the system illustrated in FIGS. 10 and 10A with respect to combining the two constituents and subsequently dispensing them is identical with the operation of the second embodiment described above with reference to FIGS. 6–9.

A fourth embodiment of the syringe system is illustrated in FIGS. 11 and 12. A number of the elements of the fourth embodiment of the syringe system are identical or functionally analogous to corresponding elements in the first embodiment illustrated in FIGS. 1–5. The elements of the fourth embodiment illustrated in FIGS. 11 and 12 are designated by three digit reference numbers between 300 and 399. The last two digits of the fourth embodiment reference numbers for elements corresponding to elements in the first embodiment are identical to the last two digits of the reference numbers used to designate those corresponding elements in the first embodiment.

With reference to FIG. 11, the fourth embodiment of the syringe system includes a first barrel 322 which has a first chamber 324 containing a first constituent 340. The lower portion of the first barrel 322 includes a delivery end or dispensing end 326 defining a delivery passage or dispensing passage 328. Preferably, the delivery passage 328 is occluded with a first, removable closure 332 which may be held in a friction fit on the delivery end 326. Other connection systems may be employed, such as snap-fit beads and grooves, threads, etc.

A reciprocable stopper 342 (which may be alternatively characterized as a moveable seal, grommet, or plunger piston) is provided above the first constituent 340 in the first chamber 324. The reciprocable stopper 342 has a lower end surface defining a conical shape 343. As shown in FIG. 11, the apex of the cone has at least one slit 389 (or two intersecting slits, not illustrated). The single slit 389 defines two lips or flaps 387. Two intersecting slits would define four lips. The lips 387 are normally biased to a closed position as illustrated in FIG. 11. The upper end of the reciprocable stopper 342 has an enlarged receiving cavity 393 and a smaller entrance passage 394 which together define a retention shoulder 395.

The reciprocable stopper 342 is initially installed in the first barrel 322 in a frictional engagement sufficient to prevent movement of the stopper during transport, storage, and handling.

The first barrel 322 may be regarded as a first container together with the reciprocable stopper 342 and closure 332 for storing the first constituent 340.

The reciprocable stopper 342 is adapted to be engaged, and moved, with a second barrel 348 which includes a cylindrical barrel portion 350 sized to be disposed in the first barrel 322.

The barrel portion 350 has a discharge end 356 defining a discharge passage 359 communicating through the discharge end 356 to accommodate the discharge of fluid from the barrel portion 350. The discharge end 356 has an enlarged head 396 and a smaller neck 398 (FIG. 11). The neck 398 and head 396 together define a transverse shoulder 399.

A liquid second constituent 346 is contained within the barrel portion 350 below a plunger 364 which has a piston 368. Preferably, in order to minimize the likelihood of contaminant ingress and to minimize the likelihood of leakage of the constituent 346, a suitable closure 362 is removably mounted to the discharge end 356. The closure 362 may be held on the discharge end 356 by means of a friction fit or by other suitable conventional or special means, such as threads, snap-fit beads and grooves, etc.

The second barrel 348 may be characterized together with the closure 362 and plunger 364 as a second container or syringe for holding and storing the liquid second constituent 346 and subsequently discharging it.

Preferably, a protective sleeve (not illustrated) may be provided for surrounding the second barrel 348 in substantially the same manner that the sleeve 52 surrounds the second barrel 48 of the first embodiment illustrated in FIG. 1.

Also, if desired, the first barrel 322 may include a removable cover (not illustrated), such as the cover 44 shown on the top of the first barrel 22 of the first embodiment illustrated in FIG. 1.

In order to use the system illustrated in FIGS. 11 and 12, the closure 362 is removed from the second barrel 348. The second barrel 348 is then disposed within the first barrel 322. Preferably, this step is accomplished by first inverting the second barrel 348 before the closure 362 is removed. The first barrel 322 is also inverted, and the two barrels are telescopically engaged in the inverted position. The second barrel 348 is pushed into the first barrel 322 until the second barrel head 396 sufficiently expands the seal entrance passage 394 and enters into the seal receiving cavity 393. In this position, the second barrel dispensing end neck 398 is received in the smaller entrance passage 394 which, owing to the resiliency of the reciprocable stopper 342, has assumed its smaller diameter configuration whereby the seal retaining flange 395 engages the second container flange 399. This prevents separation of the second barrel 348 from the first barrel reciprocable stopper 342.

In the initially engaged position, wherein the second barrel discharge end 356 is connected to the first barrel reciprocable stopper 342, the stopper lips, flaps, or valve members 387 remain closed so as to ensure that there will be no leakage of the liquid second constituent into the first constituent 340.

Subsequently, the first and second barrels are moved outwardly relative to each other, as by pushing the second barrel plunger 364 to force the liquid second constituent 346 through the valve members 387 into the first barrel first chamber 324. This forces the second barrel 348 outwardly relative to the first barrel 322.

Alternatively, the two barrels 322 and 348 may be pulled apart. Ambient air pressure acting on the plunger 368 results in the liquid second constituent 346 in the second barrel 348 being maintained under the ambient atmospheric pressure. The increasing volume of the first chamber 324 under the reciprocable stopper 342 creates a negative pressure differential, and the liquid second constituent 346 forces the valve members 387 outwardly to the open position illustrated in FIG. 12. The liquid second constituent 346 can thus flow into the first constituent 340.

The two barrels move outwardly relative to each other until the bottom surface of the plunger piston 368 engages the bottom of the cylindrical barrel portion 350 of the second barrel 348. At this point, all of the liquid second constituent 346 has been expelled into the first constituent 340 in the first chamber 324. The valve lips 387 then close. The assembly can then be shaken to ensure good mixing.

Subsequently, the closure 332 is removed from the first barrel delivery end 326. The first barrel delivery end 326 can then be connected to a receiving component or discharge tubing (not illustrated) or to a hypodermic needle (such as the needle 34 described above with reference to the first embodiment illustrated in FIGS. 1–5). Then the plunger 364 and second barrel 348 are pushed inwardly. This urges the plunger piston 368 against the bottom of the cylindrical barrel portion 350 of the second barrel 348 to move the second barrel 348 and connected reciprocable stopper 342 toward the bottom of the first container 322. This results in the combined constituents being dispensed from the first container 322.

A fifth embodiment of a syringe system, incorporating a design that may be preferred in some applications, is illustrated in FIGS. 13–16. A number of the elements of the fifth embodiment of the syringe system are identical or functionally analogous to corresponding elements in the first four embodiments illustrated in FIGS. 1–12. The elements of the fifth embodiment illustrated in FIGS. 13–16 are designated by three digit reference numbers between 400 and 499. The last two digits of the fifth embodiment reference numbers for elements corresponding to elements in the first and fourth embodiments are identical with the last two digit reference numbers used to designate those corresponding elements in the first and fourth embodiments.

With reference to FIG. 13, the preferred form of the syringe system includes a first barrel 422 which has a first chamber 424 containing a first constituent 440. The lower portion of the first barrel 422 includes a delivery end or dispensing end 426 defining a delivery passage or dispensing passage 428. Preferably, the delivery passage 428 is occluded with a first, removable closure 432 which may be held in a threaded engagement on the delivery end 426. To this end, the first barrel delivery end 426 includes a tapered luer fitment 433 surrounded by an annular collar 435 defining an interior, female thread form 436. The closure 432 includes a stem 437 for being received in the delivery passage 428 and has an exterior flange or lug 438 for engaging the female thread form 436.

A reciprocable stopper 442 is provided above the first constituent 440 in the first chamber 424. The reciprocable stopper 442 may alternatively be characterized as a moveable seal, grommet, or plunger piston. The reciprocable stopper 442 has a lower end defining an inner side or end surface 443 which has a conical shape. The apex of the cone has one slit 489. The slit 489 defines two lips or flaps 487 that are normally biased to a closed position as illustrated in solid line in FIG. 15.

The reciprocable stopper 442 has an outer side or upper end surface 439. Between the stopper outer side surface 439 and the stopper inner side surface 443 there is an enlarged receiving cavity 493 and a smaller entrance passage 494 which together define a retention shoulder 495.

The reciprocable stopper 442 is initially installed in the first barrel 422 in a frictional engagement sufficient to prevent movement of the stopper during transport, storage, and handling. The reciprocable stopper 442 is adapted to receive a support member 441.

The support member 441 defines a flow passage 445 and a communicating luer socket 444 which can receive a luer nozzle (as described hereinafter). The support member 441 has an enlarged head 496 and a smaller neck 498 (FIG. 14). The neck 498 and head 496 together define a transverse shoulder 499.

The support member 441 can be pushed into the resilient, reciprocable stopper 442 until the support member head 496 sufficiently expands the seal entrance passage 494 and enters into the seal receiving cavity 493. In this position, the support member neck 498 is received in the smaller entrance passage 494 which, owing to the resiliency of the reciprocable stopper 442, has assumed its smaller diameter configuration whereby the reciprocable stopper retaining flange 495 engages the support member shoulder 499. This prevents separation of the support member 441 from the first barrel reciprocable stopper 442. The member 441 also preferably has a support flange 457 (FIG. 14). This prevents the reciprocable stopper 442 from being deformed to the extent that it might leak.

The first barrel 422 may be characterized together with the reciprocable stopper 442, support member 441, and closure 432 as a first container for storing the first constituent 440 and for subsequently mixing it with a liquid second constituent 446 contained in a second barrel 448 (FIG. 13).

With reference to FIG. 13, the liquid second constituent 446 is contained within the cylindrical barrel portion 450 of the second barrel 448 below a plunger 464 which has a piston 468. The barrel 448 has a lower discharge end 456 defining a discharge passage 459. The discharge end 456 preferably has the configuration of a luer-type nozzle for being received in the luer-type socket 444 of the support member 441.

Preferably, in order to minimize the likelihood of contaminant ingress and to minimize the likelihood of leakage of the constituent 446, a suitable closure 462 is removably mounted to the discharge end 456. The closure 462 may be held on the discharge end 456 by means of a friction fit or by other suitable conventional or special means, such as threads, snap-fit beads and grooves, etc.

The second barrel 448 together with the closure 462 and plunger 464 may be characterized as a second container or syringe for storing and subsequently discharging the liquid second constituent 446.

Preferably, a protective sleeve (not illustrated) may be provided for surrounding the second barrel 448 in substantially the same manner that the sleeve 52 surrounds the second barrel 48 of the first embodiment illustrated in FIG. 1.

Also, if desired, the first barrel 422 may include a removable cover (not illustrated), such as the cover 44 shown on the top of the first barrel 22 of the first embodiment illustrated in FIG. 1.

In order to use the system illustrated in FIGS. 13–16, the cap 462 is removed from the second barrel 448. The second barrel 448 is then disposed within the first barrel 422. Preferably, this step is accomplished by first inverting the second barrel 448 before the closure 462 is removed. The first barrel 422 is also inverted, and the two barrels are telescopically engaged in the inverted position.

The luer-type nozzle at the discharge end 456 of the second barrel 448 is disposed within the luer-type socket 444 of the support member 441. This may be a friction fit connection. Alternatively, a more positive mechanical connection could be employed as discussed hereinafter with respect to the sixth embodiment shown in FIG. 17.

In the installed position, wherein the second barrel discharge end 456 is mounted via the member 441 to the first barrel reciprocable stopper 442, the stopper flaps, lips, or valve members 487 remain closed so as to ensure that there will be no leakage of the liquid second constituent into the first constituent 440.

The plunger 464 can be pushed to discharge the liquid second constituent 446 through the reciprocable stopper slit 489 into the first chamber 424 of the first barrel 422. As the second constituent 446 flows into the first barrel chamber 424, the reciprocable stopper 442 and second barrel 448 move outwardly. Alternatively, the first and second barrels 422 and 448 can be pulled outwardly relative to each other. Ambient air pressure acting on the plunger piston 468 results in the liquid second constituent 446 being maintained under the ambient atmospheric pressure. The increasing volume of the first chamber 424 under the reciprocable stopper 442 creates a negative pressure differential, and the liquid second constituent 446 forces the stopper lips or valve members 487 outwardly to the open position illustrated in FIG. 14. The liquid second constituent 446 can thus flow into the first constituent 440.

The two barrels 422 and 448 move outwardly relative to each other until the bottom surface of the plunger piston 468 engages the bottom of the cylindrical barrel portion 450 of the second barrel 448. At this point, all of the liquid second constituent 446 has been expelled into the first constituent 440 in the first chamber 424. The valve flaps 487 then close. The assembly can then be shaken to ensure good mixing.

Subsequently, the closure 432 is removed from the first barrel delivery end 426. The first barrel delivery end 426 can then be connected to a receiving component or discharge tubing (not illustrated) or to a hypodermic needle (such as the needle 34 described above with reference to the first embodiment illustrated in FIGS. 1–5). Then the plunger 464 is pushed inwardly. This urges the piston 468 against the bottom of the cylindrical barrel portion 450 of the second barrel 448 to move the second barrel 422, support member 441, and connected reciprocable stopper 442 toward the bottom of the first container 422. This results in the combined constituents being dispensed from the first barrel 422.

FIG. 17 illustrates a sixth embodiment of the present invention. The sixth embodiment is a modification of the fifth embodiment described above with reference to FIGS. 13–16.

In particular, the sixth embodiment includes a support member 441A generally similar to the fifth embodiment support member 441. However, the support member 441A includes an upwardly extending skirt 451A which has an internal, female thread form 453A.

A second barrel 448A is provided with a configuration generally similar to that of the fifth embodiment second barrel 448 except that the sixth embodiment second barrel 448A includes a radial lug, flange, or thread form 455A to threadingly engage the support member thread form 453A. This provides a positive mechanical connection between the second barrel 448A and the support member 441A.

In each of the fourth, fifth, and sixth embodiments illustrated in FIGS. 11–17, it is preferable to provide a clearance between the end of the head 496 of the support member 441 and the closed stopper valve lips or flaps (e.g., 487 in FIG. 16) when the stopper lips or flaps are closed. This insures that the stopper can properly collapse as far as necessary to close the slit.

The embodiments illustrated in FIGS. 11–17 may be characterized as employing a unique fluid transfer connector means or coupling means. The fluid transfer connector means or coupling means may be characterized as including (1) fluid communicating means, and (2) cooperating connecting means.

In the embodiment illustrated in FIGS. 11 and 12, the fluid communicating means include a first fluid connector in the form of a passage 359 in the second barrel discharge end 356 and a second fluid connector in the form of the flow path through the reciprocable stopper 342 and stopper flaps or lips 387. The cooperating connecting means include the enlarged head 396 on the second barrel 348 and the cooperating stopper receiving cavity 393 and retention shoulder 395.

In the embodiments illustrated in FIGS. 13–17, the fluid communicating means includes the flow passage through the reciprocable stopper 442 as well as a first fluid connector in the form of the luer-type socket or conduit 444 (FIG. 14) defining a flow passage in the support member 441 and a cooperating second fluid connector in the form of the luer-type nozzle 456 defining a flow passage in the second barrel 448. The cooperating connecting means may include just a friction-fit connection of luer-type nozzle 456 in the luer-type socket 444 as well as the engagement between the support member 441 and stopper 442. Preferably, however, as shown in FIG. 17, the connecting means also includes the thread form 453A on the support member 441A and the radial flange 455A on the second barrel 448A which cooperatively establish a threaded connection.

It will be appreciated that, in all of the embodiments illustrated, the dispensing ends or delivery ends of the first barrels are sealed with removable closures (such as the first container dispensing end closure 32). The second barrel discharge end may include a closure (i.e., closure 62 illustrated in FIG. 1). Further, such closures, if employed, may be provided in alternate forms such as threadable elastomeric seal members, flexible adhesive seal members, shrink wrap films, or other closure systems.

The above-described syringe system of the present invention provides an advantageous means for dispensing a combination of two constituents that must be kept separate from each other until they are to be used in combination. The system is self-contained and sealed. Reconstitution or dilution of a drug using this system can be effected at bedside when the drug is needed. The choice of the diluent liquid is not restricted or limited because the system accommodates any diluent compatible with the structural materials employed.

The system permits the constituents to be stored in forms in which the stability of the components is maximized. Because the reconstituted product is used immediately, provisions do not have to be made for refrigeration or other storage procedures which might otherwise be required for certain types of reconstituted products.

It will be readily apparent from the foregoing detailed description of the invention and from the illustrations thereof that numerous variations and modifications may be effected without departing from the true spirit and scope of the novel concepts or principles of this invention.

What is claimed is:

1. A syringe mixing and delivery system comprising:
   a first barrel having an open end and an opposite delivery end defining a delivery passage;
   a reciprocable stopper sealingly disposed in said first barrel to define a first chamber between said delivery passage and said reciprocable stopper for containing a first constituent in said first chamber;
   a second barrel that is sized to be disposed in said first barrel and that has an open end and an opposite discharge end defining a discharge passage;
   a slidable plunger sealingly disposed within said second barrel to define a second chamber between said discharge passage and said slidable plunger for containing a liquid second constituent in said second chamber; and
   fluid transfer connector means for operatively connecting said second barrel with said reciprocable stopper to permit flow of said liquid second constituent through said stopper from said second chamber to said first chamber to mix with said first constituent when said second barrel discharge end and plunger are moved closer together whereby subsequent movement of said second barrel and reciprocable stopper together toward said delivery passage of said first barrel expresses the mixed constituents out of said first chamber through said delivery passage.

2. The system in accordance with claim 1 wherein said fluid transfer connector means includes:
   (1) a hollow piercing needle carried by said second barrel in communication with said discharge passage; and
   (2) a portion of said reciprocable stopper being fully penetratable by said piercing needle.

3. The system in accordance with claim 1 wherein said fluid transfer connector means includes:

(1) a conduit extending through said reciprocable stopper and having an inlet end and an outlet end;

(2) a flapper valve member in said reciprocable stopper adjacent said conduit outlet end and biased to a normally closed position occluding said conduit to said conduit outlet end;

(3) a flange on said conduit inlet end; and (4) a thread form on said second barrel for being threadingly engaged by said flange whereby fluid communication is established between said discharge passage and said conduit.

4. The system in accordance with claim 1 wherein said fluid transfer connector means includes:

(1) a resilient portion defined in said reciprocable stopper and which has at least one longitudinal slit therethrough defining resilient lips which are biased to a normally closed position and which can open toward said delivery passage into said first chamber;

(2) an enlarged receiving cavity in said reciprocable stopper resilient portion adjacent said resilient lips and a smaller entrance passage in said reciprocable stopper opening into said enlarged cavity whereby a retention shoulder is defined at one end of said enlarged cavity around said smaller entrance passage; and (3) an enlarged head at said discharge passage of said second barrel for being received in said enlarged receiving cavity of said reciprocable stopper and a smaller neck at said discharge passage of said second barrel for being received in said entrance passage of said reciprocable stopper whereby said discharge passage of said second barrel is normally occluded by said biased closed resilient lips of said reciprocable stopper.

5. The system in accordance with claim 1 wherein said fluid transfer connector means includes (a) connecting means for connecting said second barrel with said reciprocable stopper, and (b) fluid communicating means permitting flow of said liquid second constituent through said stopper from said second chamber to said first chamber, said fluid communicating means comprising:

a first fluid connector associated with said reciprocable stopper in said first barrel;

a cooperating second fluid connector associated with said discharge passage of said second barrel; and a fluid passageway from said first fluid connector to said first chamber including a normally closed one way flow valve.

6. The system in accordance with claim 5 wherein said fluid passageway is defined at least in part through said reciprocable stopper; and said one way flow valve is integral with said reciprocal stopper.

7. The system in accordance with claim 6 wherein said first fluid connector includes a luer socket mounted in said reciprocable stopper in fluid communication with said one way flow valve;

said second flow connector includes a luer nozzle at said discharge passage of said second barrel; and said connecting means comprises a thread form on said second barrel proximate said luer nozzle and a radial flange on said luer socket, said radial flange being threadably engageable with said second barrel thread form for connecting said luer nozzle to said luer socket.

8. The system in accordance with claim 5 in which said first fluid connector is a support member having a luer socket that is in fluid communication with said fluid passageway;

said cooperating second fluid connector is a luer nozzle at said discharge end of said second barrel for being placed in fluid communication with said support member luer socket; and said connecting means comprises a friction fit of said second barrel luer nozzle in said support member luer socket.

9. The system in accordance with claim 8 in which said connecting means further comprises a thread form defined in said support member proximate said luer socket and a radial flange on said second barrel for threadingly engaging said support member thread form.

10. The system in accordance with claim 1 wherein said plunger includes a slidable piston and a shank mounted to said slidable piston; and said system further includes a first removable closure occluding said first barrel delivery passage; and a second removable closure occluding said second barrel discharge passage.

11. A prefilled syringe system for separately storing a first constituent and a liquid second constituent and for subsequently mixing and dispensing a mixture of said constituents, said system comprising:

a first barrel having an open end and an opposite delivery end defining a delivery passage;

a first removable closure sealingly occluding said delivery passage;

a reciprocable stopper sealingly disposed in said first barrel to define a first chamber between said delivery passage and said reciprocable stopper for containing a first constituent in said first chamber;

a second barrel that is sized to be disposed in said first barrel and that has an open end and a discharge end defining a discharge passage;

a second removable closure occluding said discharge passage;

a slidable plunger sealingly disposed within said second barrel to define a second chamber between said discharge passage and said slidable plunger for containing a liquid second constituent in said second chamber; and coupling means for operatively coupling said second barrel to said reciprocable stopper in said first barrel when said second barrel is telescopically positioned in said open end of said first barrel so that said liquid second constituent can be caused to flow through said stopper from said second chamber to said first chamber to mix with said first constituent by movement of said second barrel discharge end and plunger closer together whereby subsequent movement of said second barrel and reciprocable stopper together toward said delivery passage of said first barrel expresses the mixed constituents out of said first chamber through said delivery passage.

12. The prefilled syringe system in accordance with claim 11 in which said coupling means includes:

(1) a hollow piercing needle carried by said second barrel at said discharge passage and in fluid communication with said second chamber, and (2) a portion of said reciprocable stopper being fully penetratable by, and couplingly engageable by, said piercing needle upon removal of said second removable closure from said discharge passage of said second barrel.

13. The prefilled syringe system in accordance with claim 11 wherein said coupling means comprises
   (1) fluid communicating means for communicating fluid from said second chamber to said first chamber, and
   (2) connecting means for connecting said second barrel with said reciprocable stopper.

14. The prefilled syringe system in accordance with claim 13 in which said fluid communicating means includes
   (1) a conduit through said reciprocable stopper and having an inlet end and an outlet end;
   (2) a valve member in said reciprocable stopper adjacent said conduit outlet end and biased to a normally closed position occluding said conduit outlet end;
   (3) a first fluid connector on said conduit inlet end; and
   (4) a cooperating second fluid connector at said discharge passage of said second barrel for engaging said first fluid connector on said conduit inlet end upon removal of said second removable closure whereby fluid communication is established between said discharge passage and said conduit.

15. The prefilled syringe system in accordance with claim 14 wherein said connecting means includes a threadable flange on said first fluid connector at said conduit inlet end and a thread form on said second barrel on said cooperating second fluid connector at said discharge passage of said second barrel for being threadingly engaged by said threadable flange.

16. The prefilled syringe in accordance with claim 13 wherein
   said fluid communicating means includes a resilient portion defined in said reciprocable stopper which has at least one longitudinal slit therethrough defining resilient lips which are biased to a normally closed position and which can open toward said delivery passage into said first chamber; and
   said connecting means includes:
   (1) an enlarged receiving cavity in said reciprocable stopper resilient portion adjacent said resilient lips and a smaller entrance passage in said reciprocable stopper opening into said enlarged cavity whereby a retention shoulder is defined at one end of said enlarged cavity around said entrance passage; and
   (2) an enlarged head at said discharge passage of said second barrel received in said enlarged receiving cavity of said reciprocable stopper upon removal of said second removable closure and a smaller neck at said discharge passage of said second barrel for being received in said entrance passage of said reciprocable stopper whereby said discharge passage of said second barrel is normally occluded by said resilient lips of said reciprocable stopper in the biased closed position.

17. The prefilled syringe system in accordance with claim 11 wherein said coupling means includes
   (a) a connecting means for connecting said second barrel with said reciprocable stopper, and
   (b) a fluid communicating means for accommodating transfer of fluid from said second chamber to said first chamber, said fluid communicating means comprising:
   a first fluid connector associated with said reciprocable stopper;
   a cooperating second fluid connector associated with said discharge passage of said second barrel; and
   an openable and closeable fluid passageway from said first fluid connector in said reciprocable stopper to said first chamber of said first barrel.

18. The prefilled syringe system in accordance with claim 17 wherein
   said first fluid connector includes a stopper support member having a luer socket that is in fluid communication with said fluid passageway; and
   said cooperating second fluid connector includes a luer nozzle at said discharge passage of said second barrel for being placed in fluid communication with said support member.

19. The prefilled system in accordance with claim 18 wherein said fluid communicating means further comprises a resilient central portion defined in said reciprocable stopper which has at least one longitudinal slit therethrough defining resilient lips which are biased to a normally closed position and which can open toward said delivery passage into said first chamber to define at least a portion of said fluid passageway.

20. The prefilled syringe system in accordance with claim 19 wherein said connecting means includes
   an enlarged receiving cavity in said reciprocable stopper central portion adjacent said resilient lips and a smaller entrance passage in said reciprocable stopper opening into said enlarged cavity whereby a retention shoulder is defined at one end of said enlarged cavity around said smaller entrance passage;
   an enlarged head that is defined by said support member and that is received in said enlarged receiving cavity of said reciprocable stopper; and
   a smaller neck that is defined by said support member and that is received in said entrance passage of said reciprocable stopper wherein said fluid passageway extends through said enlarged head and smaller neck from said luer socket through said longitudinal slit whereby said discharge passage of said second barrel is normally occluded by said biased closed resilient lips of said reciprocable stopper.

* * * * *